(12) United States Patent
Choi et al.

(10) Patent No.: US 11,241,559 B2
(45) Date of Patent: Feb. 8, 2022

(54) ACTIVE DRIVE FOR GUIDEWIRE MANIPULATION

(71) Applicant: Auris Health, Inc., Redwood City, CA (US)

(72) Inventors: Inrak Choi, Stanford, CA (US); June Park, San Jose, CA (US); Arkady Kokish, Los Gatos, CA (US)

(73) Assignee: Auris Health, Inc., Redwood City, CA (US)

( * ) Notice: Subject to any disclaimer, the term of this patent is extended or adjusted under 35 U.S.C. 154(b) by 810 days.

(21) Appl. No.: 15/250,232

(22) Filed: Aug. 29, 2016

(65) Prior Publication Data

US 2018/0056044 A1  Mar. 1, 2018

(51) Int. Cl.
| | |
|---|---|
| *A61M 25/09* | (2006.01) |
| *A61B 5/00* | (2006.01) |
| *A61B 34/37* | (2016.01) |
| *A61B 34/30* | (2016.01) |
| *A61B 17/00* | (2006.01) |

(52) U.S. Cl.
CPC ..... *A61M 25/09041* (2013.01); *A61B 5/6851* (2013.01); *A61B 34/30* (2016.02); *A61B 34/37* (2016.02); *A61B 2017/00292* (2013.01); *A61B 2034/303* (2016.02)

(58) Field of Classification Search
CPC .............................................. A61M 25/09041
See application file for complete search history.

(56) References Cited

U.S. PATENT DOCUMENTS

| | | | |
|---|---|---|---|
| 2,556,601 A | | 6/1951 | Schofield |
| 2,566,183 A | | 8/1951 | Forss |
| 2,623,175 A | * | 12/1952 | Finke ............... H01Q 1/103 242/390.3 |
| 2,730,699 A | | 1/1956 | Gratian |
| 2,884,808 A | | 5/1959 | Mueller |
| 3,294,183 A | | 12/1966 | Riley et al. |

(Continued)

FOREIGN PATENT DOCUMENTS

| | | |
|---|---|---|
| CA | 2285342 A1 | 10/1998 |
| CN | 101500470 | 8/2009 |

(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

(Continued)

*Primary Examiner* — Daniel L Cerioni
*Assistant Examiner* — Yasmeen S Warsi
(74) *Attorney, Agent, or Firm* — Frost Brown Todd LLC

(57) ABSTRACT

A guidewire manipulation system may include a cylindrical drum, having a cylindrical outer drum surface with a helical groove for housing a flexible guidewire and an anchoring mechanism for attaching the flexible guidewire to the drum. The system may also include an outer shell or belt disposed around the drum, forming an opening through which the flexible guidewire exits. The system may also include a first actuator coupled with the drum for rotating the drum about a first axis, and a second actuator coupled with the drum for rotating the system about a second axis.

16 Claims, 7 Drawing Sheets

(56) References Cited

U.S. PATENT DOCUMENTS

| | | | |
|---|---|---|---|
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,784,031 A | 1/1974 | Nitu | |
| 3,790,002 A | 2/1974 | Guilbaud et al. | |
| 3,835,854 A | 9/1974 | Jewett | |
| 3,921,536 A | 11/1975 | Savage | |
| 3,926,386 A * | 12/1975 | Stahmann | B65H 49/02 242/118 |
| 4,141,245 A | 2/1979 | Brandstetter | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck et al. | |
| 4,384,493 A | 5/1983 | Grunbaum | |
| 4,507,026 A | 3/1985 | Lund | |
| 4,530,471 A | 7/1985 | Inoue | |
| 4,555,960 A | 12/1985 | King | |
| 4,688,555 A | 8/1987 | Wardle | |
| 4,745,908 A | 5/1988 | Wardle | |
| 4,784,150 A | 11/1988 | Voorhies et al. | |
| 4,857,058 A | 8/1989 | Payton | |
| 4,907,168 A | 3/1990 | Boggs | |
| 4,945,305 A | 7/1990 | Blood | |
| 4,945,790 A | 8/1990 | Golden | |
| 5,078,714 A | 1/1992 | Katims | |
| 5,207,128 A | 5/1993 | Albright | |
| 5,234,428 A | 8/1993 | Kaufman | |
| 5,256,150 A | 10/1993 | Quiachon et al. | |
| 5,277,085 A | 1/1994 | Tanimura et al. | |
| 5,339,799 A | 8/1994 | Kami et al. | |
| 5,341,807 A | 8/1994 | Nardella | |
| 5,350,101 A | 9/1994 | Godlewski | |
| 5,368,015 A | 11/1994 | Wilk | |
| 5,394,875 A | 3/1995 | Lewis et al. | |
| 5,397,443 A | 3/1995 | Michaels | |
| 5,398,691 A | 3/1995 | Martin et al. | |
| 5,408,409 A | 4/1995 | Glassman et al. | |
| 5,426,687 A | 6/1995 | Goodall et al. | |
| 5,447,529 A | 9/1995 | Marchlinski et al. | |
| 5,469,857 A | 11/1995 | Laurent et al. | |
| 5,477,856 A | 12/1995 | Lundquist | |
| 5,492,131 A | 2/1996 | Galel | |
| 5,507,725 A | 4/1996 | Savage et al. | |
| 5,524,180 A | 6/1996 | Wang et al. | |
| 5,559,294 A | 9/1996 | Hoium et al. | |
| 5,600,330 A | 2/1997 | Blood | |
| 5,631,973 A | 5/1997 | Green | |
| 5,662,108 A | 9/1997 | Budd et al. | |
| 5,673,704 A | 10/1997 | Marchlinski et al. | |
| 5,697,377 A | 12/1997 | Wittkampf | |
| 5,709,661 A | 1/1998 | Van Egmond | |
| 5,713,946 A | 2/1998 | Ben-Haim | |
| 5,722,959 A | 3/1998 | Bierman | |
| 5,738,096 A | 4/1998 | Ben-Haim | |
| 5,749,362 A | 5/1998 | Funda et al. | |
| 5,754,741 A | 5/1998 | Wang et al. | |
| 5,762,458 A | 6/1998 | Wang et al. | |
| 5,767,840 A | 6/1998 | Selker | |
| 5,779,623 A | 7/1998 | Leonard | |
| 5,784,542 A | 7/1998 | Ohm et al. | |
| 5,792,135 A | 8/1998 | Madhani et al. | |
| 5,797,900 A | 8/1998 | Madhani | |
| 5,799,055 A | 8/1998 | Peshkin et al. | |
| 5,815,640 A | 9/1998 | Wang et al. | |
| 5,825,982 A | 10/1998 | Wright et al. | |
| 5,833,608 A | 11/1998 | Acker | |
| 5,836,869 A | 11/1998 | Kudo et al. | |
| 5,836,874 A | 11/1998 | Swanson et al. | |
| 5,836,990 A | 11/1998 | Li | |
| 5,843,076 A | 12/1998 | Webster, Jr. et al. | |
| 5,845,646 A | 12/1998 | Lemelson | |
| 5,855,583 A | 1/1999 | Wang et al. | |
| 5,859,934 A | 1/1999 | Green | |
| 5,876,325 A | 3/1999 | Mizuno et al. | |
| 5,878,193 A | 3/1999 | Wang et al. | |
| 5,891,095 A | 4/1999 | Eggers et al. | |
| 5,921,968 A | 7/1999 | Lampropoulos et al. | |
| 5,925,078 A | 7/1999 | Anderson | |
| 5,935,079 A | 8/1999 | Swanson et al. | |
| 5,950,629 A | 9/1999 | Taylor et al. | |
| 5,951,475 A | 9/1999 | Gueziec et al. | |
| 5,953,683 A | 9/1999 | Hansen et al. | |
| 5,967,934 A | 10/1999 | Ishida et al. | |
| 5,983,126 A | 11/1999 | Wittkampf | |
| 6,004,271 A | 12/1999 | Moore | |
| 6,061,587 A | 5/2000 | Kucharczyk et al. | |
| 6,063,022 A | 5/2000 | Ben-Haim | |
| 6,063,095 A | 5/2000 | Wang et al. | |
| 6,077,219 A | 6/2000 | Viebach | |
| 6,080,181 A | 6/2000 | Jensen et al. | |
| 6,083,170 A | 7/2000 | Ben-Haim | |
| 6,084,371 A | 7/2000 | Kress et al. | |
| 6,096,004 A | 8/2000 | Meglan et al. | |
| 6,106,511 A | 8/2000 | Jensen | |
| 6,129,668 A | 10/2000 | Haynor et al. | |
| 6,132,368 A | 10/2000 | Cooper | |
| 6,154,000 A | 11/2000 | Rastegar et al. | |
| 6,161,032 A | 12/2000 | Acker | |
| 6,171,234 B1 | 1/2001 | White et al. | |
| 6,172,499 B1 | 1/2001 | Ashe | |
| 6,185,478 B1 | 2/2001 | Koakutsu et al. | |
| 6,203,493 B1 | 3/2001 | Ben-Haim | |
| 6,226,543 B1 | 5/2001 | Gilboa et al. | |
| 6,228,028 B1 | 5/2001 | Klein et al. | |
| 6,233,476 B1 | 5/2001 | Strommer et al. | |
| 6,233,504 B1 | 5/2001 | Das et al. | |
| 6,246,200 B1 | 6/2001 | Blumenkranz et al. | |
| 6,259,806 B1 | 7/2001 | Green | |
| 6,266,551 B1 | 7/2001 | Osadchy et al. | |
| 6,272,371 B1 | 8/2001 | Shlomo | |
| 6,289,579 B1 | 9/2001 | Viza et al. | |
| 6,301,496 B1 | 10/2001 | Reisfeld | |
| 6,309,397 B1 | 10/2001 | Julian et al. | |
| 6,310,828 B1 | 10/2001 | Mumm et al. | |
| 6,312,435 B1 | 11/2001 | Wallace et al. | |
| 6,331,181 B1 | 12/2001 | Tierney et al. | |
| 6,363,279 B1 | 3/2002 | Ben-Haim et al. | |
| 6,370,411 B1 | 4/2002 | Osadchy et al. | |
| 6,371,952 B1 | 4/2002 | Madhani et al. | |
| 6,375,471 B1 | 4/2002 | Wendlandt et al. | |
| 6,380,732 B1 | 4/2002 | Gilboa | |
| 6,381,483 B1 | 4/2002 | Hareyama et al. | |
| 6,384,483 B1 | 5/2002 | Igarashi et al. | |
| 6,393,340 B2 | 5/2002 | Funda et al. | |
| 6,394,998 B1 | 5/2002 | Wallace et al. | |
| 6,398,731 B1 | 6/2002 | Mumm et al. | |
| 6,400,979 B1 | 6/2002 | Stoianovici et al. | |
| 6,401,572 B1 | 6/2002 | Provost | |
| 6,415,171 B1 | 7/2002 | Gueziec et al. | |
| 6,424,885 B1 | 7/2002 | Niemeyer et al. | |
| 6,436,107 B1 | 8/2002 | Wang et al. | |
| 6,487,940 B2 | 12/2002 | Hart et al. | |
| 6,491,701 B2 | 12/2002 | Tierney et al. | |
| 6,493,573 B1 | 12/2002 | Martinelli et al. | |
| 6,493,608 B1 | 12/2002 | Niemeyer | |
| 6,530,913 B1 | 3/2003 | Giba et al. | |
| 6,544,230 B1 | 4/2003 | Flaherty et al. | |
| 6,550,128 B1 | 4/2003 | Lorenz | |
| 6,551,273 B1 | 4/2003 | Olson et al. | |
| 6,565,554 B1 | 5/2003 | Niemeyer | |
| 6,574,355 B2 | 6/2003 | Green | |
| 6,580,938 B1 | 6/2003 | Acker | |
| 6,587,750 B2 | 7/2003 | Gerbi et al. | |
| 6,594,552 B1 | 7/2003 | Nowlin | |
| 6,610,007 B2 | 8/2003 | Belson et al. | |
| 6,615,155 B2 | 9/2003 | Gilboa | |
| 6,618,612 B1 | 9/2003 | Acker et al. | |
| 6,620,173 B2 | 9/2003 | Gerbi et al. | |
| 6,626,899 B2 | 9/2003 | Houser et al. | |
| 6,629,534 B1 | 10/2003 | St. Goar et al. | |
| 6,659,939 B2 | 12/2003 | Moll et al. | |

(56) References Cited

U.S. PATENT DOCUMENTS

| | | |
|---|---|---|
| 6,669,709 B1 | 12/2003 | Cohn et al. |
| 6,685,698 B2 | 2/2004 | Morley et al. |
| 6,695,818 B2 | 2/2004 | Wollschlager |
| 6,699,235 B2 | 3/2004 | Wallace et al. |
| 6,716,166 B2 | 4/2004 | Govari |
| 6,726,675 B1 | 4/2004 | Beyar |
| 6,741,883 B2 | 5/2004 | Gildenberg |
| 6,774,624 B2 | 8/2004 | Anderson et al. |
| 6,783,524 B2 | 8/2004 | Anderson et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,963,792 B1 | 11/2005 | Green |
| 7,021,173 B2 | 4/2006 | Stoianovici et al. |
| 7,044,936 B2 | 5/2006 | Harding |
| 7,074,179 B2 | 7/2006 | Wang et al. |
| 7,087,049 B2 | 8/2006 | Nowlin et al. |
| 7,155,315 B2 | 12/2006 | Niemeyer et al. |
| 7,169,141 B2 | 1/2007 | Brock et al. |
| 7,172,580 B2 | 2/2007 | Hruska et al. |
| 7,225,012 B1 | 5/2007 | Susil et al. |
| 7,276,044 B2 | 10/2007 | Ferry et al. |
| 7,280,863 B2 | 10/2007 | Shachar |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 7,404,824 B1 | 7/2008 | Webler et al. |
| 7,494,494 B2 | 2/2009 | Stoianovici et al. |
| 7,540,866 B2 | 6/2009 | Viswanathan et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,850,642 B2 | 12/2010 | Moll et al. |
| 7,938,809 B2 | 5/2011 | Lampropoulos et al. |
| 7,963,288 B2 | 6/2011 | Rosenberg et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,092,397 B2 | 1/2012 | Wallace et al. |
| 8,126,534 B2 | 2/2012 | Maschke |
| 8,157,308 B2 | 4/2012 | Pedersen |
| 8,182,415 B2 | 5/2012 | Larkin et al. |
| 8,190,238 B2 | 5/2012 | Moll et al. |
| 8,202,244 B2 | 6/2012 | Cohen et al. |
| 8,219,178 B2 | 7/2012 | Smith et al. |
| 8,235,942 B2 | 8/2012 | Frassica et al. |
| 8,244,327 B2 | 8/2012 | Fichtinger et al. |
| 8,277,417 B2 | 10/2012 | Fedinec et al. |
| 8,291,791 B2 | 10/2012 | Light et al. |
| 8,343,040 B2 | 1/2013 | Frassica et al. |
| 8,414,505 B1 | 4/2013 | Weitzner |
| 8,425,465 B2 | 4/2013 | Nagano |
| 8,498,691 B2 | 7/2013 | Moll et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,870,815 B2 | 10/2014 | Bhat et al. |
| 8,894,610 B2 | 11/2014 | MacNamara et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,014,851 B2 | 4/2015 | Wong et al. |
| 9,023,068 B2 | 5/2015 | Viola |
| 9,057,600 B2 | 6/2015 | Walker et al. |
| 9,173,713 B2 | 11/2015 | Hart et al. |
| 9,204,933 B2 | 12/2015 | Reis et al. |
| 9,283,046 B2 | 3/2016 | Walker et al. |
| 9,289,578 B2 | 3/2016 | Walker et al. |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,291 B2 | 11/2016 | Balaji et al. |
| 9,498,601 B2 | 11/2016 | Tanner et al. |
| 9,504,604 B2 | 11/2016 | Alvarez |
| 9,532,840 B2 | 1/2017 | Wong et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,636,483 B2 | 5/2017 | Hart et al. |
| 9,668,814 B2 | 6/2017 | Kokish |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,123,755 B2 | 11/2018 | Walker et al. |
| 10,123,843 B2 | 11/2018 | Wong et al. |
| 10,130,345 B2 | 11/2018 | Wong et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,159,532 B1 | 12/2018 | Ummalaneni et al. |
| 10,206,746 B2 | 2/2019 | Walker et al. |
| 10,524,866 B2 | 1/2020 | Srinivasan |
| 10,543,048 B2 | 1/2020 | Noonan et al. |
| 10,639,114 B2 | 5/2020 | Schuh |
| 2001/0009976 A1 | 7/2001 | Panescu et al. |
| 2001/0029366 A1 | 10/2001 | Swanson et al. |
| 2001/0042643 A1 | 11/2001 | Krueger et al. |
| 2002/0045905 A1 | 4/2002 | Gerbi et al. |
| 2002/0087169 A1 | 7/2002 | Brock et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0138009 A1 | 9/2002 | Brockway et al. |
| 2002/0156369 A1 | 10/2002 | Chakeres |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0050649 A1 | 3/2003 | Brock et al. |
| 2003/0056561 A1 | 3/2003 | Butscher et al. |
| 2003/0073908 A1 | 4/2003 | Desai |
| 2003/0074011 A1 | 4/2003 | Gilboa et al. |
| 2003/0109780 A1 | 6/2003 | Goste-Maniere et al. |
| 2003/0135204 A1 | 7/2003 | Lee et al. |
| 2003/0212308 A1 | 11/2003 | Bendall |
| 2004/0015053 A1 | 1/2004 | Bieger |
| 2004/0034282 A1 | 2/2004 | Quaid, III |
| 2004/0034365 A1 | 2/2004 | Lentz et al. |
| 2004/0152972 A1 | 8/2004 | Hunter |
| 2004/0171929 A1 | 9/2004 | Leitner et al. |
| 2004/0176751 A1 | 9/2004 | Weitzner et al. |
| 2004/0193146 A1 | 9/2004 | Lee et al. |
| 2004/0220588 A1 | 11/2004 | Kermode et al. |
| 2004/0243147 A1 | 12/2004 | Lipow |

(56) References Cited

U.S. PATENT DOCUMENTS

| | | |
|---|---|---|
| 2004/0254566 A1 | 12/2004 | Plicchi |
| 2005/0004579 A1* | 1/2005 | Schneider ......... A61M 25/0105 606/108 |
| 2005/0027397 A1 | 2/2005 | Niemeyer |
| 2005/0059960 A1 | 3/2005 | Simaan et al. |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0177026 A1 | 8/2005 | Hoeg et al. |
| 2005/0182295 A1 | 8/2005 | Soper et al. |
| 2005/0182330 A1 | 8/2005 | Brockway et al. |
| 2005/0183532 A1 | 8/2005 | Najaf et al. |
| 2005/0200324 A1 | 9/2005 | Guthart et al. |
| 2005/0203382 A1 | 9/2005 | Govari et al. |
| 2005/0222554 A1 | 10/2005 | Wallace et al. |
| 2006/0013523 A1 | 1/2006 | Childers et al. |
| 2006/0025676 A1 | 2/2006 | Viswanathan et al. |
| 2006/0025679 A1 | 2/2006 | Viswanathan et al. |
| 2006/0041245 A1 | 2/2006 | Ferry |
| 2006/0058647 A1 | 3/2006 | Strommer et al. |
| 2006/0111692 A1 | 5/2006 | Hlavka et al. |
| 2006/0146010 A1 | 7/2006 | Schneider |
| 2006/0178556 A1 | 8/2006 | Hasser et al. |
| 2006/0200049 A1 | 9/2006 | Leo et al. |
| 2006/0201688 A1 | 9/2006 | Jenner et al. |
| 2006/0229587 A1 | 10/2006 | Beyar et al. |
| 2006/0229641 A1 | 10/2006 | Gupta et al. |
| 2006/0237205 A1 | 10/2006 | Sia et al. |
| 2006/0271036 A1 | 11/2006 | Garabedian et al. |
| 2007/0000498 A1 | 1/2007 | Glynn et al. |
| 2007/0013336 A1 | 1/2007 | Nowlin et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0123851 A1 | 5/2007 | Alejandro et al. |
| 2007/0149946 A1 | 6/2007 | Viswanathan |
| 2007/0156123 A1 | 7/2007 | Moll et al. |
| 2007/0185486 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0249901 A1 | 10/2007 | Ohline et al. |
| 2007/0287999 A1 | 12/2007 | Malecki et al. |
| 2007/0293724 A1 | 12/2007 | Saadat et al. |
| 2007/0299427 A1 | 12/2007 | Yeung et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0039255 A1 | 2/2008 | Jinno et al. |
| 2008/0046122 A1 | 2/2008 | Manzo et al. |
| 2008/0064920 A1 | 3/2008 | Bakos et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0183071 A1 | 7/2008 | Strommer et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0300592 A1 | 12/2008 | Weitzner et al. |
| 2008/0302200 A1 | 12/2008 | Tobey |
| 2008/0319311 A1 | 12/2008 | Hamadeh |
| 2009/0054884 A1 | 2/2009 | Farley et al. |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0131872 A1 | 5/2009 | Popov |
| 2009/0137952 A1 | 5/2009 | Ramamurthy et al. |
| 2009/0163948 A1 | 6/2009 | Sunaoshi |
| 2009/0171371 A1 | 7/2009 | Nixon |
| 2009/0221908 A1 | 9/2009 | Glossop |
| 2009/0247944 A1 | 10/2009 | Kirschenman et al. |
| 2009/0248039 A1 | 10/2009 | Cooper et al. |
| 2009/0318797 A1 | 12/2009 | Hadani |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081920 A1 | 4/2010 | Whitmore, III et al. |
| 2010/0130923 A1* | 5/2010 | Cleary ............... A61M 25/0113 604/95.04 |
| 2010/0130987 A1 | 5/2010 | Wenderow et al. |
| 2010/0175701 A1 | 7/2010 | Reis et al. |
| 2010/0187740 A1 | 7/2010 | Orgeron |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0016346 A1 | 1/2012 | Steinmetz et al. |
| 2012/0046652 A1 | 2/2012 | Sokel |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1* | 9/2012 | Bhat ................. A61B 1/00147 604/95.01 |
| 2012/0239012 A1 | 9/2012 | Laurent et al. |
| 2012/0245595 A1 | 9/2012 | Kesavadas et al. |
| 2012/0277730 A1 | 11/2012 | Salahieh |
| 2012/0283747 A1 | 11/2012 | Popovic |
| 2012/0310112 A1 | 12/2012 | Fichtinger et al. |
| 2012/0316393 A1 | 12/2012 | Frassica et al. |
| 2013/0012779 A1 | 1/2013 | Frassica et al. |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0257334 A1 | 9/2014 | Wong et al. |
| 2014/0264081 A1 | 9/2014 | Walker et al. |
| 2014/0276233 A1 | 9/2014 | Murphy |
| 2014/0276389 A1 | 9/2014 | Walker |
| 2014/0276392 A1 | 9/2014 | Wong et al. |
| 2014/0276394 A1 | 9/2014 | Wong et al. |
| 2014/0276594 A1 | 9/2014 | Tanner et al. |
| 2014/0276646 A1 | 9/2014 | Wong et al. |
| 2014/0276934 A1 | 9/2014 | Balaji et al. |
| 2014/0276935 A1 | 9/2014 | Yu |
| 2014/0276936 A1 | 9/2014 | Kokish et al. |
| 2014/0276937 A1 | 9/2014 | Wong et al. |
| 2014/0276938 A1 | 9/2014 | Hsu et al. |
| 2014/0276939 A1 | 9/2014 | Kokish et al. |

(56) References Cited

U.S. PATENT DOCUMENTS

| | | |
|---|---|---|
| 2014/0277333 A1 | 9/2014 | Lewis et al. |
| 2014/0277334 A1 | 9/2014 | Yu et al. |
| 2014/0277747 A1 | 9/2014 | Walker et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133858 A1 | 5/2015 | Julian et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0223902 A1 | 8/2015 | Walker et al. |
| 2015/0231364 A1 | 8/2015 | Blanchard |
| 2015/0265807 A1 | 9/2015 | Park et al. |
| 2015/0297864 A1 | 10/2015 | Kokish et al. |
| 2015/0314110 A1 | 11/2015 | Park |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2015/0375399 A1 | 12/2015 | Chiu et al. |
| 2016/0000512 A1 | 1/2016 | Gombert et al. |
| 2016/0001038 A1 | 1/2016 | Romo et al. |
| 2016/0157945 A1 | 6/2016 | Madhani |
| 2016/0166234 A1 | 6/2016 | Zhang |
| 2016/0192860 A1 | 7/2016 | Allenby |
| 2016/0202053 A1 | 7/2016 | Walker et al. |
| 2016/0206389 A1 | 7/2016 | Miller |
| 2016/0213435 A1 | 7/2016 | Hourtash |
| 2016/0213884 A1 | 7/2016 | Park |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0065356 A1 | 3/2017 | Balaji et al. |
| 2017/0071684 A1 | 3/2017 | Kokish et al. |
| 2017/0100084 A1 | 4/2017 | Walker et al. |
| 2017/0100199 A1 | 4/2017 | Yu et al. |
| 2017/0105804 A1 | 4/2017 | Yu |
| 2017/0113019 A1 | 4/2017 | Wong et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0209672 A1 | 7/2017 | Hart et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0116735 A1 | 5/2018 | Tierney et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0086087 A1 | 3/2020 | Hart et al. |
| 2020/0091799 A1 | 3/2020 | Covington et al. |

(56) References Cited

U.S. PATENT DOCUMENTS

| | | |
|---|---|---|
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155245 A1 | 5/2020 | Yu |
| 2020/0155801 A1 | 5/2020 | Kokish |

FOREIGN PATENT DOCUMENTS

| | | |
|---|---|---|
| CN | 103037799 | 4/2011 |
| CN | 102316817 | 1/2012 |
| CN | 102458295 | 5/2012 |
| CN | 102665590 | 9/2012 |
| CN | 102973317 | 3/2013 |
| CN | 102015759 | 4/2013 |
| CN | 103735313 | 4/2014 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2567670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | 9744089 A1 | 11/1997 |
| WO | 0011495 A1 | 3/2000 |
| WO | 0045193 A1 | 8/2000 |
| WO | WO 02/074178 | 9/2002 |
| WO | 03077769 A1 | 9/2003 |
| WO | 03086190 A1 | 10/2003 |
| WO | 03091839 A2 | 11/2003 |
| WO | 2005087128 A1 | 9/2005 |
| WO | WO 07/146987 | 12/2007 |
| WO | WO 09/092059 | 7/2009 |
| WO | WO 11/005335 | 1/2011 |
| WO | 2012037506 A2 | 3/2012 |
| WO | WO 13/179600 | 12/2013 |
| WO | 2014028699 A1 | 2/2014 |
| WO | 2014028702 A1 | 2/2014 |
| WO | WO 15/127231 | 8/2015 |
| WO | WO 17/059412 | 4/2017 |
| WO | WO 17/0151993 | 9/2017 |

OTHER PUBLICATIONS

Amendment & Response to Non-Final Office Action for related U.S. Appl. No. 11/678,016, filed with the United States Patent and Trademark Office Dec. 27, 2010 (21 pages).

European Search Report for European Patent Application No. 14160068.4, dated Feb. 6, 2015 (6 pages).

European Search Report for European Patent Application No. 14160078.3, dated Feb. 11, 2015 (6 pages).

Non-Final Office Action for related U.S. Appl. No. 11/678,016, dated Aug. 31, 2010 (30 pages).

European Office Action European Application No. 07757358.2, dated Dec. 9, 2008 (3 pages).

Chinese Office Action for Chinese Application No. 200780006359.8, dated Aug. 9, 2010, in Chinese language with translation provided by Chinese associate (6 pages).

International Preliminary Report on Patentability for International Patent Application No. PCT/US2007/062617, dated Aug. 26, 2008 (7 pages).

International Search Report for International Patent Application No. PCT/US2006/026218, dated Dec. 12, 2006 (2 pages).

International Search Report for International Patent Application No. PCT/US2005/007108, dated Jun. 27, 2005 (4 pages).

Written Opinion of the International Searching Authority for International Patent Application No. PCT/US2006/026218, dated Dec. 12, 2006 dated Dec. 12, 2006 (7 pages).

Written Opinion of the International Searching Authority for International Patent Application No. PCT/US2005/007108, dated Jun. 27, 2005 (6 pages).

* cited by examiner

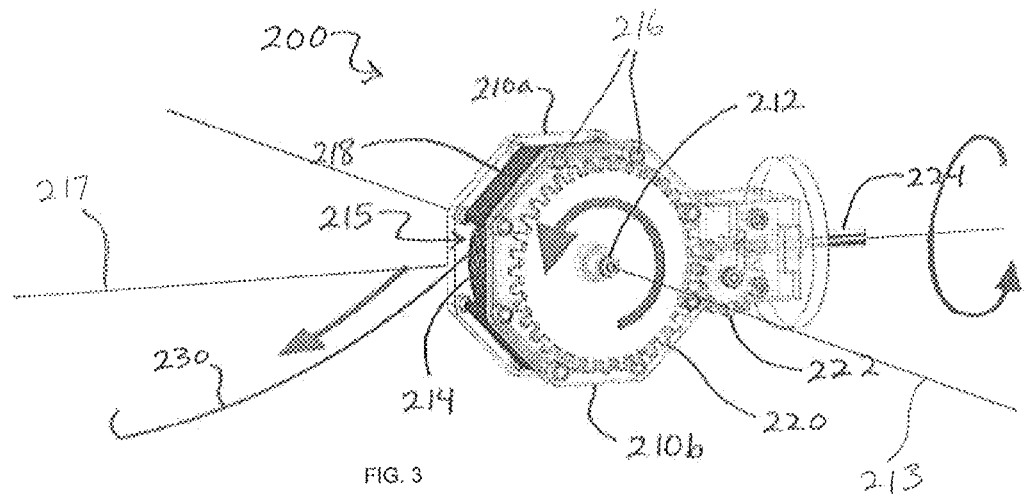
FIG. 3
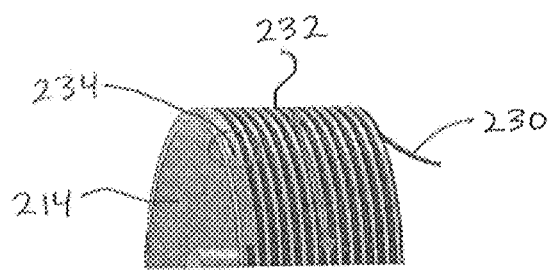
FIG. 4A
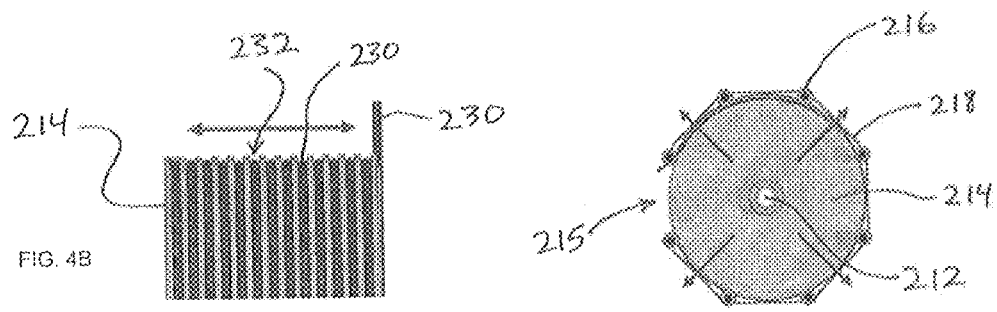
FIG. 4B
FIG. 4C

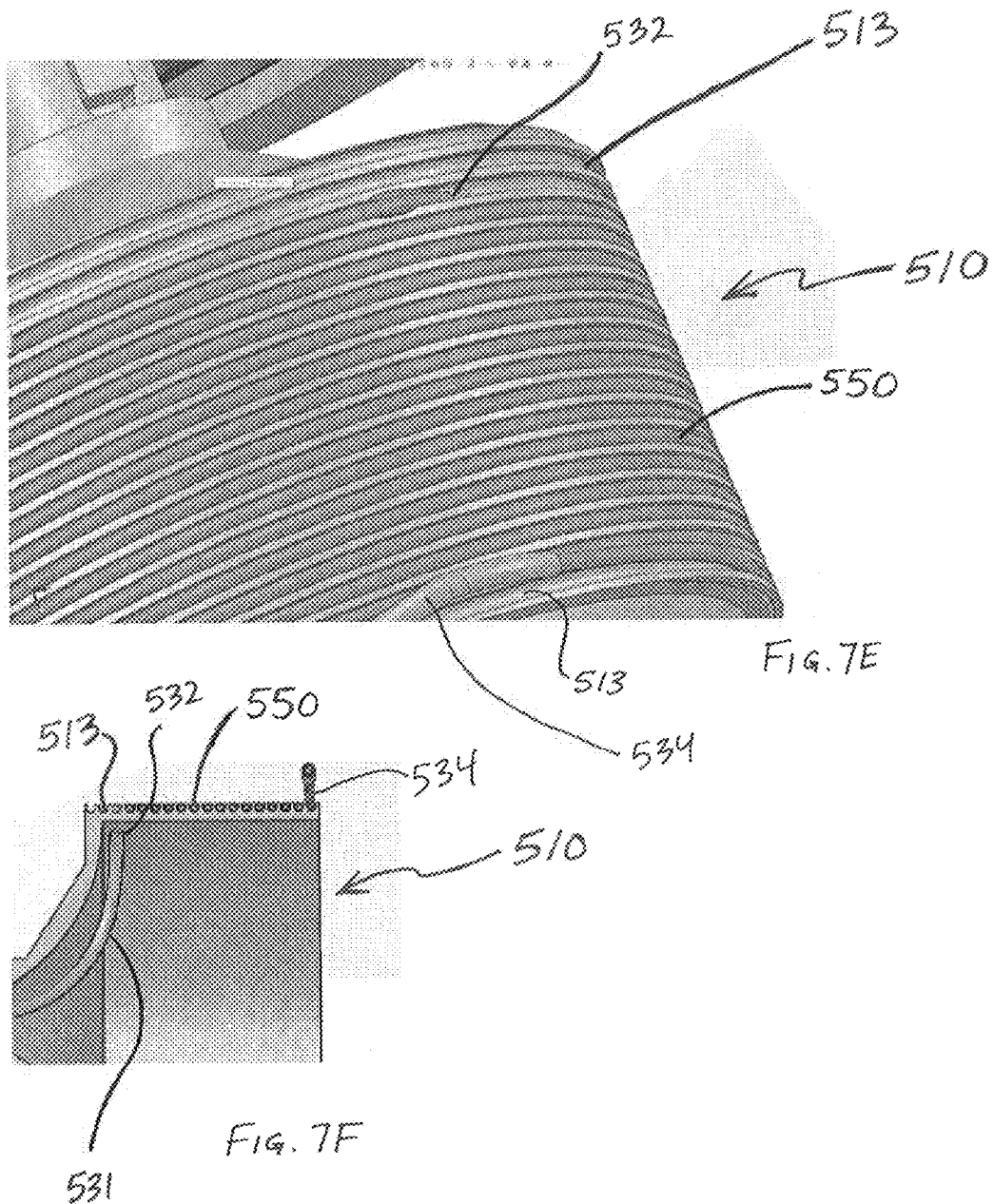

ACTIVE DRIVE FOR GUIDEWIRE MANIPULATION

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to the surgical robotics field. More specifically, the invention relates to a new and useful system and method for robotically manipulating a guidewire.

BACKGROUND

Advances in technology have led to significant changes in the practice of medicine and surgery. Less invasive medical and surgical procedures are increasingly popular, and in particular, surgical techniques referred to as minimally invasive surgery (MIS) are rapidly gaining popularity. MIS is generally defined as surgery that is performed by entering the body through the skin, a body cavity, or an anatomical opening, using small incisions rather than large, open incisions in the body. With MIS, it is possible to achieve less operative trauma for the patient, reduced hospitalization time, less pain and scarring, reduced incidence of complications related to surgical trauma, lower costs, and/or a speedier recovery, as compared to traditional, open surgical techniques.

A number of MIS procedures and non-surgical interventional procedures are performed using catheters that are advanced through blood vessels to an area of the body to be treated. The catheter used to gain access to the body is sometimes used in performing the procedure itself, and in other cases, one or more various instruments are advanced through the catheter to perform the procedure. A wide array of procedures on the heart and blood vessels, for example, are now performed using these catheter-based, endovascular or transvascular techniques. For this reason, steerable catheters are widely used for navigating through vasculature. It can be very challenging to precisely control the distal end (or tip) of a long, thin, and flexible catheter by manipulating the proximal end of the catheter, which remains outside the patient during the procedure. A slight mistake in catheter manipulation can also have very serious consequences, such as a tear or dissection in the blood vessel wall. As such, physicians typically advance small, floppy guidewires into the blood vessel first, to explore the area of interest, and then advance a catheter over the guidewire. Guidewire manipulability is thus essential to the success of most endovascular and transvascular procedures.

As part of the advance in MIS techniques, robotic interventional systems have been developed and have become quite popular. Some of these robotic systems have been developed specifically for catheter-based procedures. These catheter-based robotic systems typically involve manipulation of catheters and guidewires. MIS devices and techniques have advanced to the point where an insertion and rolling motion of elongate members, such as a catheter sheath and associated guidewire, are generally controllable by selectively operating rollers or other mechanisms for gripping the elongate members. Although many improvements in robotic catheter and guidewire manipulation have been made, robotic guidewire manipulation remains a challenge. The challenge arises, because guidewires are generally very thin, floppy, long and slippery. Guidewires often are coated with a hydrophilic coating, which makes them even more slippery when the hydrophilic coating is activated by saline or blood. Furthermore, in some clinical applications, doctors need to be able to insert the guidewire while simultaneously rolling it. This creates a spiraling motion on the tip of the guidewire, which is often preferred by doctors to reduce friction and potentially enable better control. The need for simultaneous insertion and rotation capabilities limits the design solutions for this problem. For example, a three-jaw chuck is a conventional method for grabbing small cylindrical objects to rotate them, but this jaw design does not allow for simultaneous and infinite insertion.

In addition, guidewires often do not have very high torsional stiffness, due to their long length (typically >200 cm) and small diameter (typically <1 mm). The guidewire is often advanced deep into tortuous anatomy, so high rotation torques are required to overcome bending along its length and deliver necessary torques to the tip of the guidewire. Rotation of a non-torsionally stiff guidewire (e.g., a torsionally flexible guidewire) through this tortuous anatomy often requires several rotations (i.e., wind up) at the proximal end before the distal end rotates. In addition, the distal tip will often whip past the target location, and the doctor may need to continue to rotate the guidewire several times to get the tip to the correct location. In order to address these challenges, it is desirable to have a guidewire manipulator that can allow for infinite rotations of the proximal end of the guidewire.

In addition, the surgical procedure needs to be performed in a sterile space. The robot used in these procedures is typically non-sterile. A sterile drape is placed over the robot before the robot is placed in the sterile field. Therefore, the motors in the robot used to drive a guidewire manipulation device need to transfer motion through a sterile barrier.

Although various gripping and manipulating devices have been developed for robotic catheter systems, it can still be challenging to adequately grip, advance, infinitely rotate, simultaneously insert and rotate, and generally manipulate a guidewire through a sterile barrier, using a robotic system.

Therefore, a need exists for improved devices, systems, and methods for manipulating elongate, flexible devices in robotic MIS surgical systems. Ideally, such devices, systems, and methods would be able to grip elongate, flexible instruments, specifically guidewires, and advance retract, infinitely rotate, simultaneously advance and rotate, and otherwise manipulate them with minimal slippage, through a sterile barrier. At least some of these objectives will be addressed by the embodiments described herein.

BRIEF SUMMARY

Various embodiments presented herein involve a cylindrical drum, which forms at least a portion of a guidewire manipulation system. In various embodiments, a guidewire may be wrapped onto the surface of the cylindrical drum prior to or during a procedure, and the drum may then be rotated to unwrap the guidewire and insert it into the patient. In addition, the whole drum may be rotated about a different axis to rotate the guidewire. The embodiments provided herein remove the need to grip the guidewire to generate traction, because in the provided designs, the back end of the guidewire is anchored to the drum, and the friction between the drum and the guidewire provides additional traction to prevent slippage when advancing and retracting the guidewire. Several embodiments of this design are presented herein.

One aspect of this disclosure is directed to a guidewire manipulation system for translating and rotating a flexible guidewire for a medical or surgical procedure. The system may include a cylindrical drum, a guiding layer disposed around the drum and defining an opening through which the flexible guidewire passes, a first actuator coupled with the drum for rotating the drum about a first axis, to translate the guidewire through the opening and along a longitudinal axis of the guidewire, and a second actuator coupled with the drum for rotating the drum about a second axis, to roll the guidewire about the longitudinal axis. The cylindrical drum may include a cylindrical outer drum surface with a helical groove for housing the flexible guidewire and an anchoring mechanism for attaching the flexible guidewire to the drum. For example, in some embodiments, the anchoring mechanism may include an opening near one of the edges of the outer drum surface and a channel in communication with the opening that narrows down to a diameter sufficiently small to fixedly hold the flexible guidewire when it is inserted therein.

In some embodiments, the system may also include two discs coupled with the cylindrical drum at opposite edges of the outer drum surface and multiple rods disposed between the two discs above the outer drum surface. In such embodiments, the guiding layer may be a belt disposed around at least some of the rods, such that the opening is defined by a space between two of the multiple rods between which the belt does not extend. In some embodiments, the belt may be a loop wrapped around the rods, so that it rolls over the rods with frictional force from the flexible guidewire as the flexible guidewire is translated through the opening.

Optionally, the system may also include a covering for the opening, configured to close the opening during at least part of a procedure in which the system is used. In some embodiments, the first actuator and the second actuator are disposed in an actuator base coupled with the cylindrical drum. In some embodiments, the cylindrical drum may be removable from the system without dissembling the system. Such embodiments may optionally include a replacement drum, and the helical groove of the drum and a helical groove of the replacement drum may have different sizes to accommodate different sizes of guidewires.

In some embodiments, the guiding layer may be a cylindrical shell configured to move axially along the cylindrical drum as the drum is rotated. Such embodiments may optionally also include a cylindrical outer housing disposed over the cylindrical drum, a first tubular channel extending from a proximal end of the outer housing to a proximal edge of the cylindrical drum to guide the flexible guidewire from the proximal end of the outer housing to the proximal edge of the drum, and a second tubular channel extending from a distal edge of the drum to a distal end of the outer housing, to guide the flexible guidewire from the distal edge of the drum to the distal end of the outer housing. Such embodiments may also include a first guide tube for guiding the guidewire from the proximal end of the outer housing to the helical groove at the proximal edge of the drum and a second guide tube for guiding the guidewire from the helical groove at the distal edge of the drum to the distal end of the outer housing. Other optional features of such embodiments include: (1) a cylindrical barrel disposed between the outer housing and the cylindrical drum, where the drum and the barrel are configured to rotate relative to the outer housing and to each other; (2) a first drive shaft coupled with the drum for rotating the drum about a central axis of the drum and the outer housing, to advance and retract the guidewire along a longitudinal axis of the guidewire; (3) a second drive shaft coupled with the barrel for rotating the barrel about the central axis to roll the guidewire about the longitudinal axis; (4) a proximal clamp for clamping the guidewire at or near a proximal end of the outer housing; and (5) a distal clamp for clamping the guidewire at or near a distal end of the outer housing. In some embodiments, the cylindrical barrel comprises an inner threaded surface that meshes with a complementary outer threaded surface on the first drive shaft. Optionally, the cylindrical drum may be configured to move in a first direction within the cylindrical barrel when the system winds the guidewire onto the cylindrical drum and in a second direction within the cylindrical barrel when the system unwinds the guidewire off of the cylindrical drum.

Another aspect of this disclosure is directed to a method for translating and rotating a flexible guidewire for a medical or surgical procedure on a patient. The method may involve: fixedly attaching one end of a guidewire to a rotating, cylindrical drum within a housing; rotating the drum in a first direction to wind at least part of the guidewire onto a helical groove on an outer surface of the drum; rotating the drum in a second, opposite direction to unwind at least part of the guidewire off of the drum and thus advance the guidewire into the patient; and spinning the housing to roll the guidewire.

In some embodiments, the method may also include guiding the guidewire onto the helical groove on the outer surface of the drum with a belt disposed over the drum. In some embodiments, rotating the drum may involve rotating a first drive shaft coupled with the drum, and spinning the drum may involve rotating a second drive shaft coupled with the drum. The method may also involve clamping a first clamp at a first end of the housing during winding of the guidewire onto the drum, releasing the first clamp, and clamping a second clamp at a second end of the housing during unwinding of the guidewire off of the drum. In some embodiments, spinning the drum may involve spinning a barrel disposed around the drum.

These and other aspects and embodiments are described in greater detail below, in reference to the attached drawing figures.

BRIEF DESCRIPTION OF THE DRAWINGS

FIG. 3 is a perspective view of a guidewire manipulation system, according to one embodiment;

FIGS. 4A-4C are perspective, front-end and side views, respectively, of portions of the guidewire manipulation system of FIG. 3;

FIGS. 7E and 7F are perspective and side, cross-sectional views, respectively, of a portion of the guidewire manipulation system of FIGS. 7A-7D.

DETAILED DESCRIPTION

Figure 1:
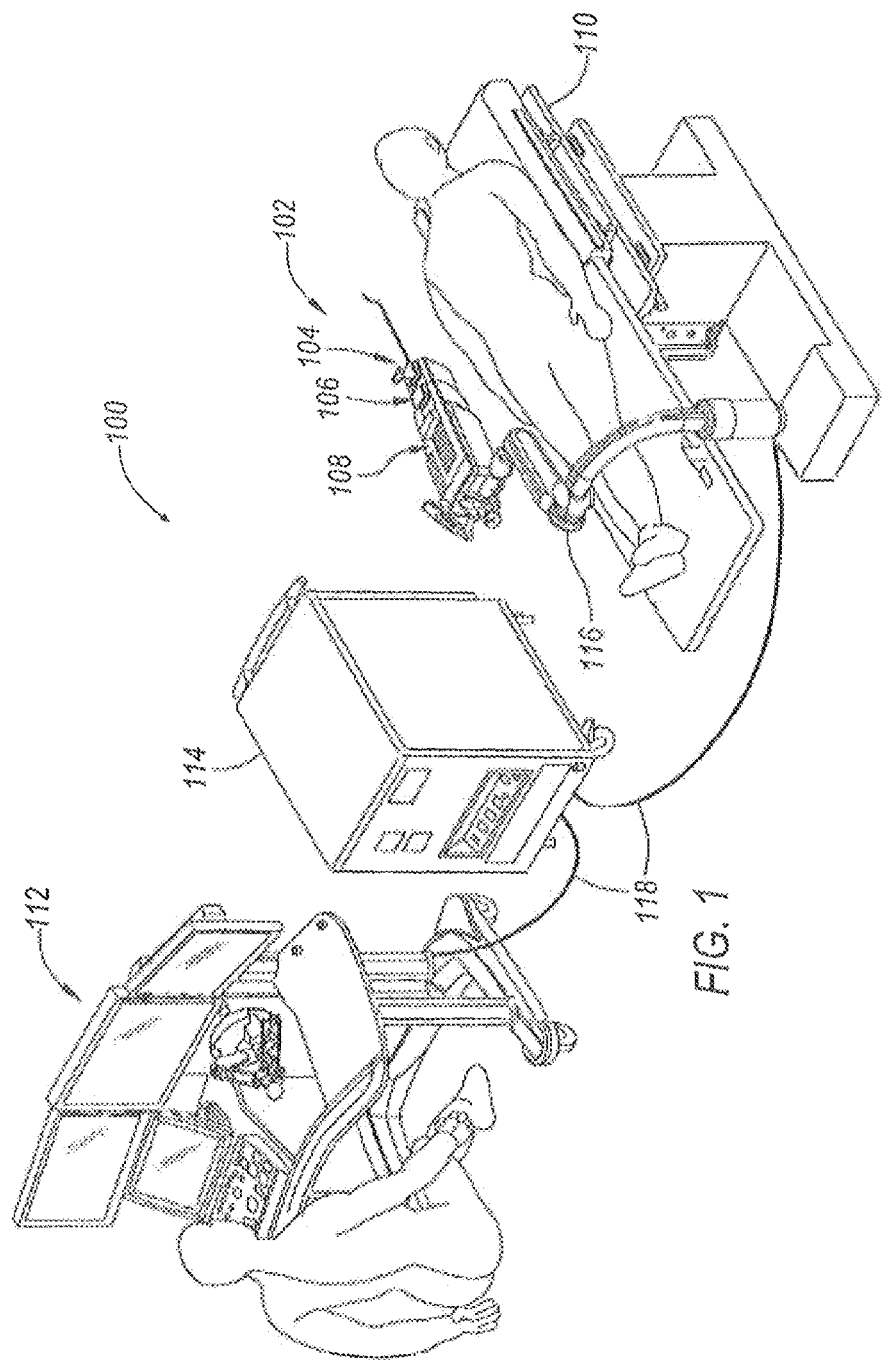
FIG. 1 is an illustration of a robotically controlled surgical system, according to one exemplary illustration.

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Referring to FIG. 1, one embodiment of a robotically controlled surgical system 100 is illustrated. System 100 may include a robotic catheter assembly 102, having a first or outer steerable complement, otherwise referred to as a robotic sheath or sheath instrument 104 (also referred to simply as a "sheath") and/or a second or inner steerable component, otherwise referred to as a robotic catheter, guide or catheter instrument 106 (also referred to simply as a "catheter"). Catheter assembly 102 is controllable using a robotic instrument driver 108. During use, a patient is positioned on an operating table or surgical bed 110, to which robotic instrument driver 108 may be coupled or mounted. In the illustrated example, system 100 includes an operator workstation 112, an electronics rack 114, and an associated bedside electronics box (not shown), a setup joint mounting brace 116, and instrument driver 108. A physician (or "operator") sits at operator workstation 112 and can monitor the surgical procedure and patient vitals and control one or more catheter devices. Operator workstation 112 may include a computer monitor to display the catheter instrument or component thereof, e.g., a guidewire and/or a catheter sheath. In some cases, the catheter instrument may be imaged via fluoroscopy and displayed within, or relative to a body cavity, organ, or part of an organ, e.g., a chamber of a patient's heart.

System components may be coupled together via cables or other suitable connectors 118 to provide for data communication. In some embodiments, one or more components may be equipped with wireless communication components to reduce or eliminate cables 118. Communication between components may also be implemented over a network or over the Internet. In this manner, a surgeon or other operator may control a surgical instrument while being located away from or remotely from radiation sources, such as the fluoroscopy system (e.g., behind a shield or partition), thereby decreasing radiation exposure. With the option for wireless or networked operation, the surgeon may even be located remotely from the patient in a different room or building.

System 100 typically includes one or more mechanisms for advancing and retracting (i.e., "translating") catheter assembly instruments into and out of a patient and for rotating the catheter assembly instruments while and/or after they are translated. Applicant for the present application has developed a number of such mechanisms, which are sometimes referred to generally as "active drive mechanisms." One example of such an active drive mechanism is described in U.S. Patent Application Publication Number 2014/0276936, now abandoned, which is hereby incorporated by reference in its entirety. Typically, active drive mechanisms developed thus far have used one or more pairs of belts or rollers to manipulate a guidewire. For example, the guidewire may be gripped between two rollers, and when the active drive mechanism rotates the rollers about their individual axes of rotation, they advance and retract the guidewire into and out of the patient. The active drive mechanism may also cause the pair of rollers as a whole to rotate about a longitudinal axis of the guidewire to cause the guidewire to rotate about its longitudinal axis. This is important, because it is often necessary to translate and rotate a guidewire as it is advanced into a patient, in order to direct the distal end of the guidewire to a desired location.

As mentioned above, although rollers work well in some situations, they often work less well for hydrophilic guidewire manipulation. The main challenge stems from the fact that the guidewire manipulator is trying to grip something that is inherently slippery. To firmly grasp a guidewire, two rollers are pressed together to generate a large grasping force. Once enough friction force is generated between guidewire 550 and the rollers, the guidewire manipulator can insert and roll the guidewire by moving the rollers. The large amount of pressing force required between the two rollers, however, may cause joints of the active drive mechanism to wear down quickly. Also, the slippery hydrophilic coating on the guidewire requires even greater application of force between the rollers, and even with this force, it is still difficult to prevent the guidewire from slipping between the rollers. In addition, the large amount of force may damage the hydrophilic coating on the guidewire. Given the importance of reliable guidewire manipulation during an interventional medical/surgical procedure, these challenges with currently available systems are significant.

Figure 2A:
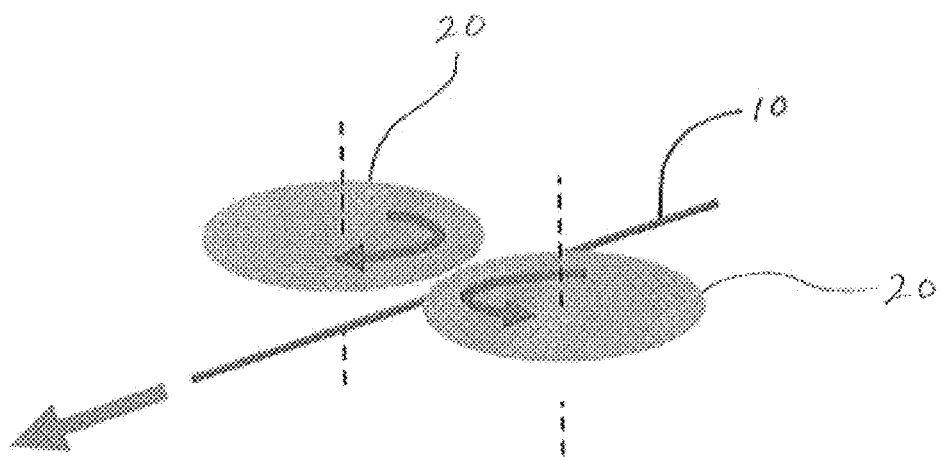
FIG. 2A is a schematic illustration of a prior art guidewire manipulation device.
Figure 2B:
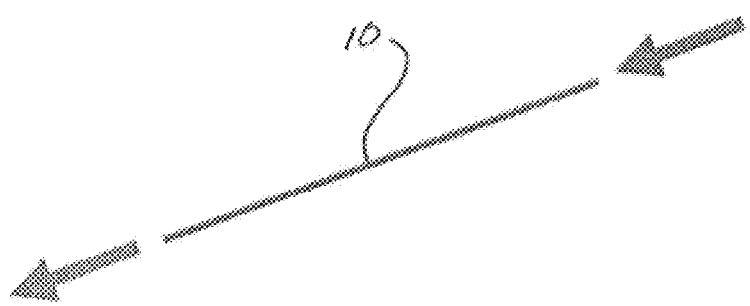
FIG. 2B is a schematic illustration of a guidewire manipulation device, according to one embodiment.

Referring now to FIGS. 2A and 2B, a fundamental difference between prior art guidewire manipulation devices (FIG. 2A) and those described in this disclosure (FIG. 2B) is illustrated schematically. In FIG. 2A, a guidewire 10 passes through the two friction driving wheels 20. When wheels 20 are pressed together, the friction between guidewire 10 and driving wheels 20 generates force to advance or retract guidewire 10. Guidewire 10 may tend to slip, however, at the driving wheel interface, due to a large amount of resistance from the tortuous blood vessel anatomy through which it is being advanced. The problem gets worse when guidewire 10 is coated with hydrophilic material, as it makes guidewire 10 more slippery. The only currently available solution is to tighten the grip by squeezing wheels 20 harder together. It is not possible to fully prevent slippage, however, no matter how much pressure is applied, and added pressure puts a great deal of stress on the guidewire manipulation system.

FIG. 2B schematically illustrates an improved method for manipulating a guidewire 10, which will be described in further detail below. Rather than using friction-generating wheels, the improved method advances and retracts guidewire 10 by pushing and pulling it, respectively, from its back end, where guidewire 10 is anchored to the drive system. Since guidewire 10 is pushed and pulled to advance and retract it, rather than being fed through two wheels, there is no guidewire slippage. How this method is achieved, and various embodiments of guidewire manipulation systems used to achieve the method, are described in greater detail below.

Referring now to FIG. 3, one embodiment of a guidewire manipulation system 200 is illustrated. In this embodiment, system 200 includes an outer housing made up of two discs 210a, 210b connected by multiple rods 216 extending between them, an inner drum 214 sandwiched between the two discs 210a, 210b, a belt 218 wrapped around at least some of the rods 216 to form one continuous band that substantially covers inner drum 214 except at an opening 215 between two of the rods 216, and an axle 212. Axle 212 defines an insertion axis 213 about which inner drum 214 rotates. A disc gear 220 may be mounted on axle 212 on an inner or outer surface of disc 210a or disc 210b, and disc gear 220 may have gear teeth, which mesh with complementary gear teeth on a drive gear 222 of the system 200. Rotation of drive gear 222 induces rotation of disc gear 220 and rotationally-coupled inner drum 214 about the insertion axis 213 defined by axle 212 (illustrated by large, counterclockwise arrow on disc gear 220). Such rotation causes a guidewire 230 to unwind (i.e., advance) or wind up (i.e., retract). System 200 may include a drive shaft 224 or other mechanism to couple to an actuator on the instrument driver. These features of guidewire manipulation system 200 will be described in further detail below.

In use, one end of guidewire 230 is attached (or "anchored") to inner drum 214 by one of any number of suitable anchoring means. Inner drum 214 is then rotated in a first direction—clockwise in FIG. 3—and such rotation wraps guidewire 230 around inner drum 214. Inner drum 214 has a continuous, spiral groove 232 (FIGS. 4A and 4B), and guidewire 230 fits within groove 232 as it wraps around inner drum 214. Once guidewire 230 is wrapped, inner drum 214 can be rotated counterclockwise, as illustrated by the curved arrow in FIG. 3, which causes guidewire 230 to unwind and advance out of opening 215 and into the patient, as illustrated by the relatively straight arrow in FIG. 3. If guidewire 230 needs to be retracted, inner drum 214 can be rotated again in the clockwise (or "winding") direction.

Because guidewire 230 is anchored at one end to inner drum 214, frictional force, such as the opposing wheels of prior art systems, is not required for advancing and retracting guidewire 230. Thus, guidewire slippage is no longer an issue. In fact, the friction between guidewire 230 and inner drum 214 helps retract the guidewire. When inner drum 214 is rotated in the clockwise direction to wind guidewire 230, guidewire 230 is naturally pressed against inner drum 214 as guidewire 230 is pulled in by the rotating inner drum 214, increasing friction as a result. In this case, the friction is evenly distributed along the portion of guidewire 230 making contact with inner drum 214, and the widely distributed friction helps secure guidewire 230 during its retraction phase. When inner drum 214 is rotated in the counterclockwise direction to unwind guidewire 230, it is no longer pressed against inner drum 214, and the friction between guidewire 230 and inner drum 214 is greatly reduced, which helps advance guidewire 230 with minimum effort.

When a procedure using guidewire manipulation system 200 is complete, guidewire 230 may be easily removed from inner drum 214. The system 200 may then be disposed of or cleaned, re-sterilized, and used for a next procedure.

Referring now to FIGS. 4A-4C, several features of system 200 are illustrated in greater detail. FIG. 4A is a perspective view of a portion of inner drum 214, showing guidewire 230 lying in groove 232 of inner drum 214. In the embodiment shown, groove 232 is one, continuous, spiral groove. In alternative embodiments, groove 232 may be multiple side-by-side grooves or have any other suitable configuration for partially housing guidewire 230 on the surface of inner drum 214. FIG. 4A also illustrates one possible guidewire anchoring mechanism in the form of a slot 234. Slot 234 may lead into a bore that tapers down to a smaller diameter, so that a user may insert one end of guidewire 230 into slot 234 and advance it with sufficient force until it becomes stuck. Any other suitable anchoring mechanism may be used in alternative embodiments, such as hooks, holes, clips, fasteners or the like, independently or in addition to slot 234.

FIG. 4B is a front-end view of a portion of inner drum 214, illustrating groove 232 in greater detail. Groove 232 is an important feature of at least some embodiments of inner drum 214, because it controls how guidewire 230 is wrapped in a spiral onto inner drum 214, and without it, guidewire 230 may wind upon itself and get entangled or slide laterally along the surface of drum 214, and thus increase the risk of guidewire 230 buckling within system 200.

FIG. 4C is a side view of a portion of system 200. Belt 218 is wrapped around rods 216 in a conveyor belt-like fashion. Except for a space 215 located between one set of two adjacent rods 216, belt 218 wraps around an entirety of inner drum 214, forming a loop having an inner layer that hugs inner drum 214 and an outer layer separated from the inner layer by the diameter of rods 216. The two adjacent rods 216 defining space 215 serve as axles or pivot points around which belt 218 wraps in order to form the loop.

The purpose of belt 218 is to hold guidewire 230 within (and prevent it from lifting off of) groove 232 of inner drum 214 as guidewire 230 is advanced through opening 215 and inserted into the patient. By maintaining guidewire 230 within groove 232, the wound portion of guidewire 230 does not bulge, bubble, or otherwise significantly loosen around inner drum 214, and the rotating motion of inner drum 214 is efficiently translated into the inserting motion of guidewire 230. In this embodiment, belt 218 rolls over rods 216 as guidewire 230 advances. This is caused by the frictional force of guidewire 230 moving against belt 218 as it is advanced. Allowing belt 218 to roll over rods 216 prevents excess friction between guidewire 230 and belt 218 as guidewire 230 is advanced out of opening 215. If belt 218 did not roll, or if it were replaced by a rigid static cylindrical housing, the guidewire 230 would drag on the belt or housing as the inner barrel 214 rotated, causing unwanted friction and potentially inhibiting advancement of guidewire 230 and/or scraping off some of the hydrophilic coating on guidewire 230. If belt 218 were replaced by a housing that rotated with the guidewire to reduce friction, then the opening 215 would also rotate. This would not be a desirable solution, since it is desired to keep the opening in a constant location to feed the guidewire into the catheter or patient. As such, employing a flexible belt 218 to hold guidewire 230 in groove 232 helps minimize the adverse effect of friction, while allowing the exit location of guidewire 230 to remain stationary. In addition, the manufacturing of flexible belt 218 is not excessively restricted by the selection of belt material. If flexible belt 218 is made of slippery material, guidewire 230 may slide against belt 218, which is acceptable as long as belt 218 can hold guidewire 230 in groove 232 during operation. If the friction between flexible belt 218 and guidewire 230 becomes large, belt 218 will start rolling over rods 216, naturally preventing friction from building up. In some embodiments, belt 218 rolls over rods 216, and rods 216 remain static and do not move. In alternative embodiments, rods 216 may be free to spin when belt 218 rolls over them. For example, rods 216 may be mounted with ball bearings to allow them to freely spin/roll.

In the embodiment shown, system 200 includes eight rods 216, but alternative embodiments may include different numbers of rods 216 with different spacing. Any suitable number and spacing of rods 216 may be selected. It may be desirable to select a number and spacing of rods 216 that prevent the inner portion/layer of belt 218 from contacting the outer portion/layer of belt 218. Such contact may cause unwanted friction, which may put a strain on guidewire manipulation system 200. If an embodiment has fewer, more widely spaced rods 216, it may be advantageous to have a tighter belt 218, relative to an embodiment having more, closer-spaced rods 216. The tighter belt may limit belt deformation and unintended contact between the two layers of belt 218. In some embodiments, guidewire manipulation system 200 may include a tensioner (not shown), to keep belt 218 taut, in order to apply force against the expanding guidewire 230, to keep it in groove 232. Belt 218 may be made of any suitable material such as, but not limited to, silicone or polyurethane. Because belt 218 is not subjected to large frictional forces (in contrast to the friction wheels described above), and it functions adequately regardless of whether it is slippery, the range of possible materials for belt 218 is relatively large, potentially lowering the cost of manufacturing.

Figure 5:
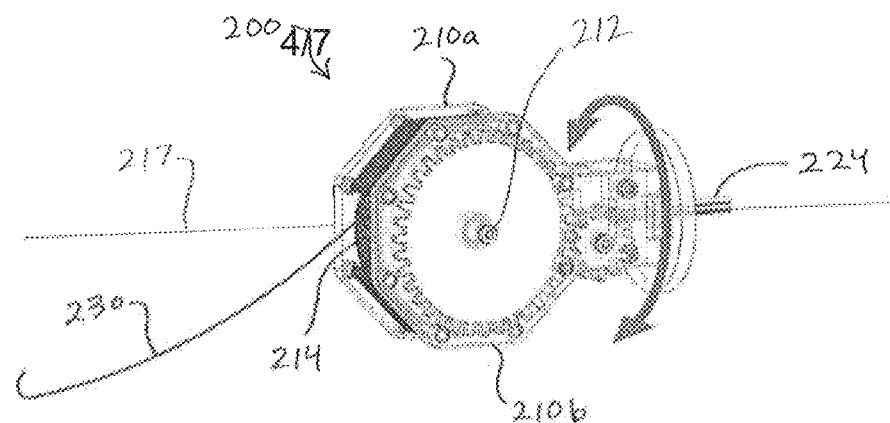
FIG. 5 is a perspective view of the guidewire manipulation system of FIG. 3, illustrating rotation of the entire system for rolling a guidewire.

Referring now to FIG. 5, as mentioned previously, a guidewire manipulation system, such as system 200, should generally be configured to advance and retract guidewire 230 and also to spin or rotate guidewire 230 about its longitudinal axis 217. This spinning motion is important, because that is often how guidewire 230 is directed or steered within a patient. This rolling or spinning motion is depicted in FIG. 5 by the curved, double-headed arrow.

Figure 6:
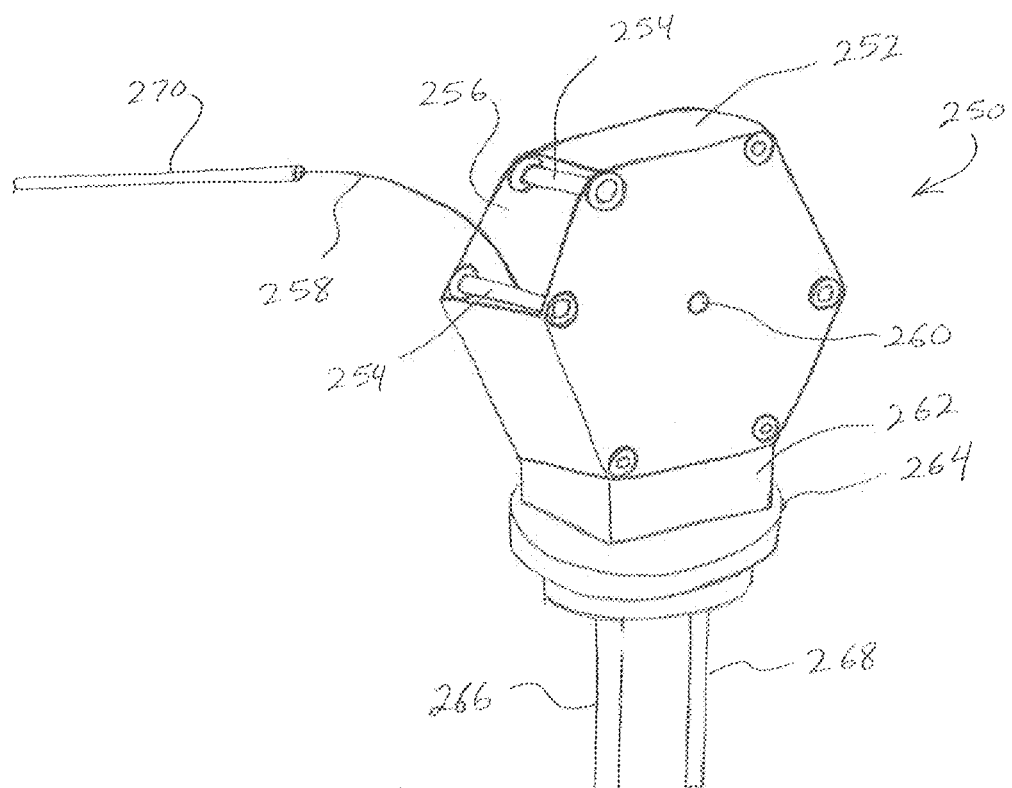
FIG. 6 is a perspective view of a guidewire manipulation system, according to an alternative embodiment.

In an alternative embodiment, as shown for example in FIG. 6, a guidewire manipulation system 250 may include an outer housing 252 with an opening 256 through which a guidewire 258 exits, multiple rods 254, an axle 260, a gear box, a flange coupler 264 a first drive shaft 266 and a second drive shaft 268. The internal workings of system 250, within housing 252, such as the drum and the belt, may be the same or similar to the inner workings of the embodiment of system 200 describe in FIGS. 3-5. In this embodiment, however, two drive shafts 266, 268 extend from gearbox 262. First drive shaft 266 (similar to drive shaft 224 in FIG. 3) is configured for rolling the inner drum (not visible in FIG. 6 but analogous to inner drum 214 of FIGS. 3-5) about axle 212 to translate (i.e., insert and retract) guidewire 258. Second drive shaft 268 is configured for rotating the entire outer housing 252 relative to flange coupler 264, thus spinning guidewire 258 about its longitudinal axis. All of system 250 may be coupled at one end, via flange coupler 264, to an instrument driver of a robotic surgical system. Flange coupler 264 may contain a bearing or bushing to allow rotation of assembly 250 without excessive drag. Drive shafts 266, 268 may be connected to one or more actuators, such as an electric motor of a larger system, such as the instrument driver of a robotic surgical system described above. Drive shafts 266, 268 may be keyed or slotted to correspond with a mating feature in the instrument driver. The design shown has a male coupler on the guidewire manipulation system 250, which is configured to be received by a female coupler on the instrument driver. Alternatively, guidewire manipulation system 250 may have a recess or female coupler and the protruding shaft or male coupler may be on the instrument driver. Alternatively, the connection between the system 250 and the instrument driver may contain a sterile adapter such as that disclosed in U.S. Pat. No. 8,720,448.

The rotation of the inner drum about the translation axis may be activated with or without movement of the outer housing about the roll axis and vice versa. The translation mechanism and roll mechanism are independent and may be activated in isolation, in series/sequence, or in parallel/simultaneously. That means rotation of the guidewire in either direction may be achieved without any insertion or retraction of the guidewire or may occur in conjunction with insertion or retraction of the guidewire to get a spiraled trajectory on the wire.

In some embodiments, opening 215 on one side of guidewire manipulation system 200 may be covered during an operation, to prevent guidewire 230 from buckling and expanding outward. A small, curved cover (not shown) may be included in system 200, to guide the guidewire through opening 215 without buckling, for example.

Additionally, system 200 may be configured to accommodate multiple different sizes of guidewires 230. Since guidewires 230 come in a variety of different diameters, and since guidewire 230 should fit well within groove 232, it may be desirable in some embodiments to provide inner drums 214 with differently sized grooves 232. One embodiment of guidewire manipulation system 200, for example, may include a separate, interchangeable inner drum 214 for each of a number of different guidewire sizes. For example, a 0.014" guidewire 230 could be used with an inner drum 214 that has a smaller groove 232 relative to an inner drum 214 used with a 0.035" guidewire 230. In some embodiments, the physician or other user may be able to quickly exchange one inner drum 214 for another in system 200, similar to exchanging a cartridge in a printer. In an alternative embodiment, only one inner drum 214 may be provided, and it may have a groove 232 that is large enough to accommodate the largest guidewire 230 suitable for use with system 200. When a smaller guidewire 230 is used, it may wiggle slightly in groove 232. However, belt 218 may be tightened using a tensioner and/or configured suitably to hold the smaller guidewire 230 within the larger groove 232. Such a belt 218 may be thick enough and/or compliant enough to also accommodate larger-diameter guidewires 230. In this embodiment, therefore, one inner drum 214 may be used with multiple different sizes of guidewires.

In some embodiments, guidewire manipulation system 200 (or system 250 or other alternative embodiments) may be directly plugged into the driving axes of a robotic surgery system, as described above in relation to FIG. 1. System 200, 250 may optionally include a flexible tube 270 (FIG. 6), which acts as a channel from guidewire manipulation system 200, 250 to the back of a catheter splayer 104, 106, so that guidewire 230, 258, as it exits system 200, 250 may be smoothly guided into the catheter. In some embodiments, such flexible tube 270 may be fixed to the back of the splayer with a freely rotating cuff, so that it does not twist when guidewire manipulation system 200, 250 rotates to roll guidewire 230, 258. Flexible tube 270 may float or slide across opening 215, 256 to accommodate guidewire 230, 258 entering into or exiting from different grooves as the inner drum rotates.

Referring now to FIGS. 7A-7F, an alternative embodiment of an active drive guidewire manipulation system 500 is illustrated. As in the previously described embodiment, guidewire manipulation system 500 includes a rotating inner drum 510 around which a guidewire 550 is wound, and to which guidewire 550 is anchored. As in other embodiments, inner drum 510 is located within a housing 540. Additionally, as in other embodiments, guidewire 550 is loaded entirely onto inner drum 510 at the start of a procedure, inner drum rotates 510 about its own axis (i.e., the translation axis, which is the same as guidewire 550 in FIG. 7A) to insert or retract guidewire 550 into the patient, and the entire housing 540 rotates (i.e., about the roll axis) to rotate or spin guidewire 550. In this embodiment of system 500, however, inner drum 510 is oriented differently, relative to guidewire 550 and a patient, than the inner drum 214 of the previously described embodiment of guidewire manipulation system 200. In guidewire manipulation system 200, the translation axis 213 (about which inner drum 214 rotates) is perpendicular to the translating guidewire 230 and the roll axis 217, whereas in guidewire manipulation system 500, the translation axis (about which inner drum 510 rotates) is collinear with the translating guidewire 550 and the roll axis.

Figure 7A:
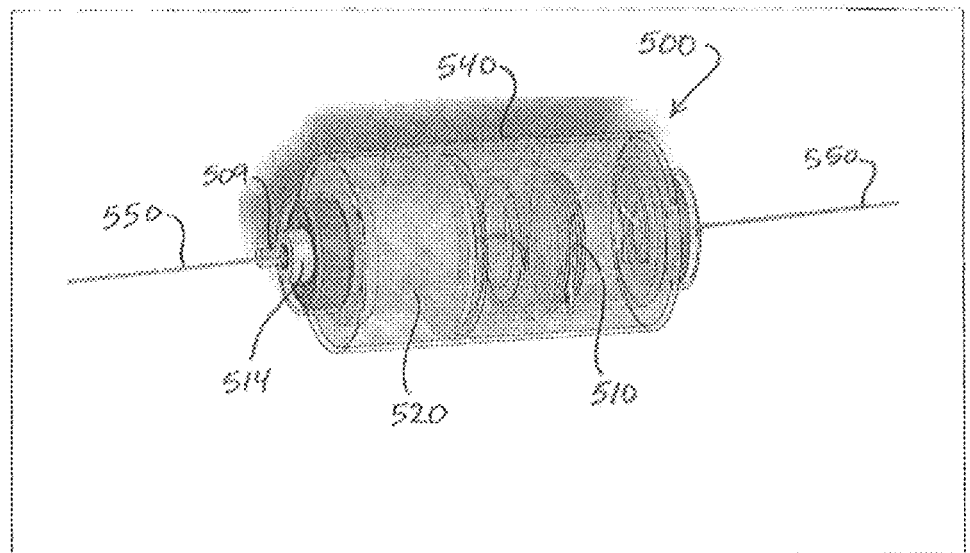
FIGS. 7A and 7B are perspective views of a guidewire manipulation system, according to another alternative embodiment
Figure 7B:
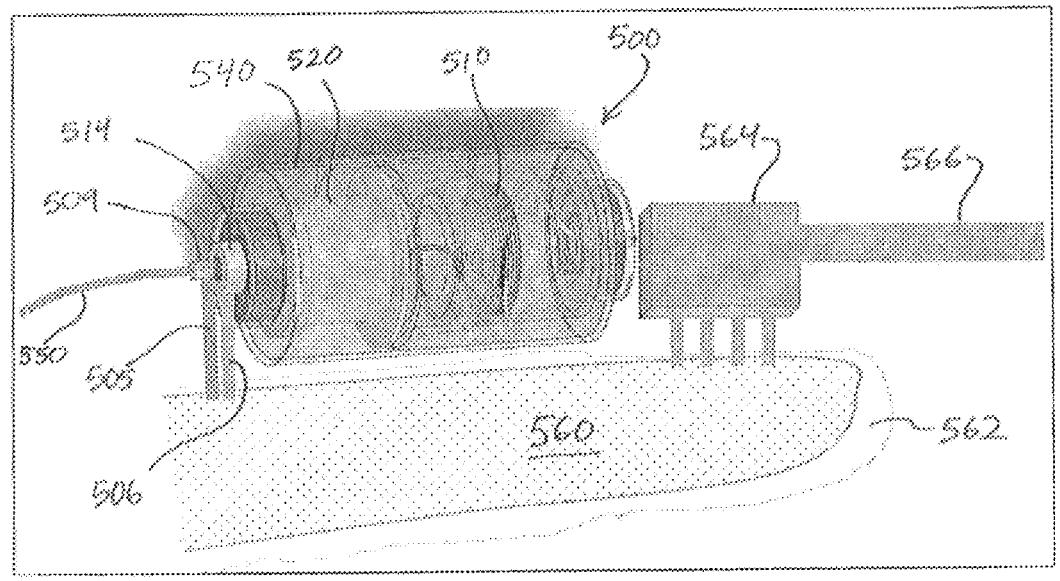
Figure 7C:
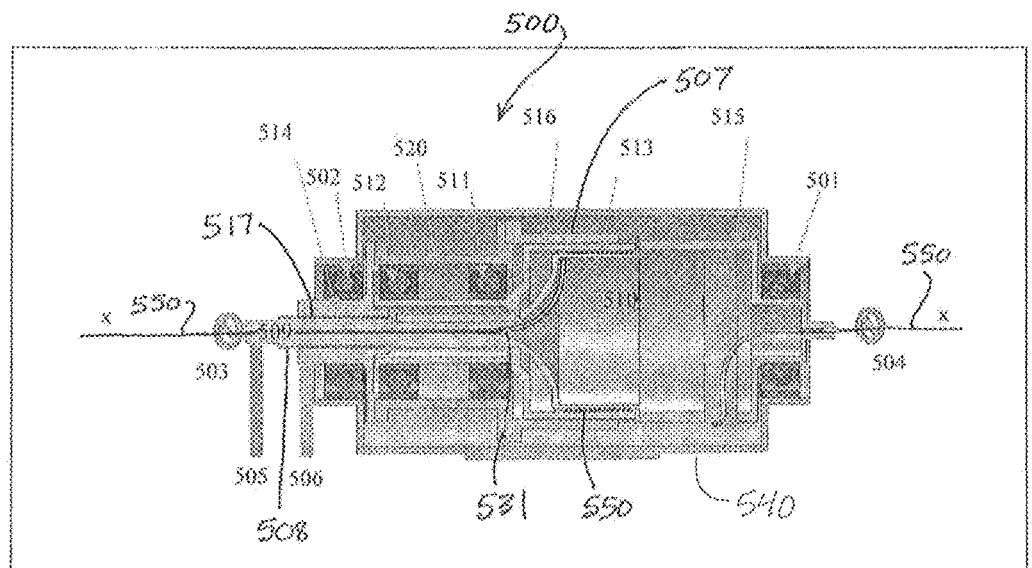
FIGS. 7C and 7D are side, cross-sectional views of the guidewire manipulation system of FIGS. 7A and 7B.
Figure 7D:
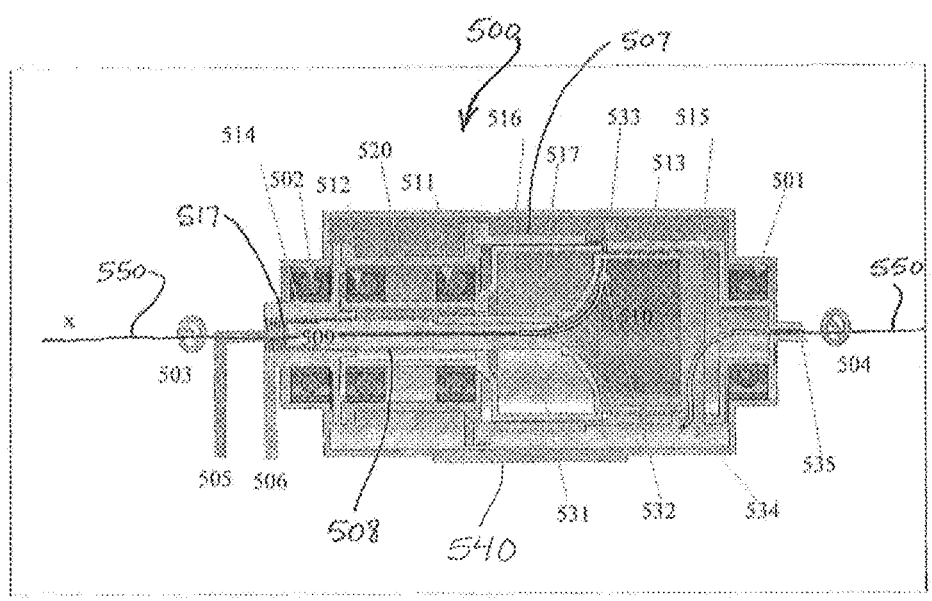

FIG. 7A is a perspective view of system 500. FIG. 7B is also a perspective of system 500, shown attached to adjacent components of a robotic catheter system (such as the system shown in FIG. 1). FIG. 7C is a side cross-sectional view of system 500 with guidewire 550 loaded onto it, and FIG. 7D is the same side cross-sectional view with guidewire 550 fully advanced out of system 500 (e.g., toward a patient). Because the various components of guidewire manipulation system 500 may be seen most clearly in the cross-section figures, those figures will be described first.

Referring to FIG. 7C, guidewire manipulation system 500 is illustrated with guidewire 550 fully loaded onto inner drum 510. Inner drum 510 and most of the other components of system 500 are at least partially housed within outer housing 540. Outer housing 540 contains bearings 501 and 502 on either end, which allow inner drum 510 to rotate within (and relative to) outer housing 540 about a central axis XX. Between outer housing 540 and inner drum 510 there is a a second actuator, in the form of an inner barrel 507, which also rotates relative to housing 540. When inner barrel 507 rotates, guidewire 550 and everything inside inner barrel 507 rotates. In the embodiment shown, inner barrel 507 is made of three connected parts 514, 515 and 520. This configuration is not required, however, and in alternative embodiments, inner barrel 507 may be a one-piece component or may have any other suitable number of parts. Guidewire 550 enters the assembly at a proximal opening along the central axis XX and through proximal clamp 503; it passes through a spiraled path guiding tube 531 to the outside of inner drum 510; it winds around the barrel multiple times (not visible in a cross-sectional view); it exits inner drum 510 in another spiraled path guiding tube; and then it exits the assembly along the central axis XX at a distal opening, passing through distal clamp 504.

In this embodiment, a cylindrical shell 516 is located between inner barrel 507 and inner drum 510 and is connected to a first actuator, in the form of a drive shaft 509, via a key 517. Shell 516 rotates with inner drum 510 to reduce friction. Shell 516 does not move from left to right or right to left during loading or unloading of guidewire 550 onto inner drum 510. Its purpose is to rotate with inner drum 510 to help prevent friction between the rotating guidewire 550 (on inner drum 510) and inner barrel 507. Shell 516 serves the same purpose as belt 218 in mechanism 200. It ensures the guidewire wraps smoothly onto and off of the inner drum, and it rolls with the inner drum to reduce friction. Thus, various embodiments described herein include a guiding layer (e.g., belt 218 or shell 516), which substantially surrounds the inner drum to facilitate smooth wrapping and unwrapping of the guidewire onto and off of the inner drum, and which moves or rotates when the inner drum rotates so as not to create significant friction against the inner drum.

Inner drum 510 is located inside inner barrel 507. Inner drum 510 rotates with respect to inner barrel 507 via support bearings 511 and 512. Similar to system 200, in at least some embodiments of system 500, inner drum 510 contains a grooved surface 513 to allow guidewire 550 to wrap around it. Inner drum 510 is connected to a drive shaft 509, which has a threaded outer surface 508, which mates with a corresponding threaded surface 517 on housing inner barrel 507.

Before starting a guidewire-based procedure, guidewire 550 is loaded onto inner drum 510. To load inner drum 510, guidewire 550 is manually loaded from the proximal end of system 500, through an opened proximal clamp 503. Proximal clamp 503 and a distal clamp 504 are shown schematically in FIGS. 7C and 7D. In at least one embodiment of system 500, clamps 503, 504 are attached to opposite ends of inner barrel 507. Guidewire 550 passes through drive shaft 509 and into the proximal end of a first, inner drum guiding tube 531. As shown more clearly in FIGS. 7E and 7F, the distal end of first, inner drum guiding tube 531 is attached to inner drum 510 at point 532, to direct guidewire 550 tangentially onto the outer surface groove 513 of inner drum 510. In the loading configuration, inner drum 510 is positioned such that when guidewire 550 exits first guiding tube 531 at point 532, it is guided into an inner barrel groove 513. Inner barrel groove 513 continues to spiral around the outer surface of inner barrel 510. When guidewire 550 reaches a second guiding tube 534, it passes through it and exits inner 510 and housing 540 at point 535, through distal clamp 504. After guidewire 550 is manually advanced through system 500, distal clamp 504 is closed, and proximal clamp 503 remains open. The remainder of guidewire 550 is now loaded robotically onto inner drum 510. This is accomplished by commanding a rotation to drive shaft 505, which rotates drive shaft 509 of inner drum 510. The connection between drive shafts 505 and 509 is shown only schematically in FIG. 7D, but this connection may be any connection capable of transferring motion through a 90° turn, such as a bevel gear connection.

When inner drum 510 turns and the distal end of guidewire 550 is locked in distal clamp 504, guidewire 550 becomes wrapped onto inner drum 510. The pitch of the spiral path for guidewire 550 on inner drum 510 matches the pitch of the thread on drive shaft 509. Therefore, as drive shaft 509 and inner drum 510 are rotated to further load guidewire 550 onto inner drum 510, inner drum 510 moves from the right side of inner barrel 507 (FIG. 7D) to the left side of inner barrel 507 (FIG. 7C), as viewed from the vantage point of the provided figures. That is, inner drum 510 moves proximally. The outlet point for the guidewire from inner drum 510 to inner barrel 507 at point 532 does not move during the loading process. As drive shaft 509 continues to rotate, guidewire 550 is wrapped onto inner drum 510. The number of revolutions of inner drum 510 is based on the length of guidewire 550. The diameter of inner drum 510 depends on the stiffness, size and material of guidewire 550 and in some embodiments may range from approximately 2 inches to approximately 4 inches.

Referring to FIG. 7C, when guidewire 550 is fully loaded onto inner drum 510, proximal clamp 503 may be closed to lock the back end of guidewire 550 to inner barrel 507. Now guidewire manipulation system 500 is ready for use in a guidewire based procedure. Next, distal clamp 504 may be opened. To insert guidewire 550 into the patient or a catheter, inner drum 510 may then be rotated in the opposite direction of the loading direction. Shell 516 ensures that guidewire 550 is wrapped tightly onto inner drum 510. If no shell 516 were present, rotation of inner drum 510 in the opposite direction of the loading direction would simply cause guidewire 550 to lift off the surface of inner drum 510. But the presence of shell 516 prevents this and so would instead cause guidewire 550 to "unload" back out the proximal side of system 500. For clarification, rotating inner drum 510 in the non-loading direction with clamp 503 open and distal clamp 504 closed would undo the loading process. When proximal clamp 503 is closed and distal clamp 504 is open, rotating inner barrel 510 in the non-loading direction causes guidewire 550 to move out of the right (i.e., distal) side of system 500 and into the patient or catheter.

Groove 513 on inner drum 510 and the clearance between inner drum 510 and shell 516 are sized to accommodate the outer diameter of guidewire 550. This helps ensure that there will not be backlash when the user changes the direction of guidewire 550 (e.g., from advancing into the patient to retracting out of the patient or vice versa). When insertion or retraction of guidewire 550 is commanded, drive shaft 505 turns, which rotates drive shaft 509, to cause guidewire 550 to spool onto, or unspool off of, the surface of inner drum 510. In this system 500, with the insertion axis and drive shaft 509 collinear with the translating guidewire 550, rotation of shaft 509 to create insertion/retraction of guidewire 550 would typically cause guidewire 550 to rotate as it is being inserted or retracted. To prevent this from occurring, drive shaft 506, which causes inner barrel 507 to rotate to roll guidewire 550, will rotate in the opposite direction of shaft 505, thereby eliminating the effect of the rotation from the translation axis. Therefore, shafts 505 and 506 turn in opposite directions at appropriate speeds, if guidewire insertion or retraction without rotation is commanded by the robotic surgical system. At one or more points during a procedure, a physician may want to only rotate (or "spin" or "roll") guidewire 550. When only wire rotation is desired, then only drive shaft 506 rotates. When insertion and rotation are desired at the same time, either drive shaft 505 may rotate by itself or both drive shafts 505, 506 may rotate, with shaft 506 acting to increase or decrease the speed of rotation.

At the end of a procedure, the user may close distal clamp 504 and lift guidewire manipulation system 500 off (or out of) the surgical robotic system with which it is being used and remove it from guidewire 550, allowing inner drum 510 to unspool free as system 500 is moved away. Alternatively, inner drum 510 may be rotated to unspool guidewire 550.

Referring back to FIG. 7B, guidewire manipulation system 500 is illustrated on a schematic representative of an instrument driver 560. Instrument driver 560 may be identical to instrument driver 108 in FIG. 1 or may be an alternative embodiment. A schematic representation of a catheter 566, catheter splayer 564, guidewire 550, instrument driver 560, and sterile drape 562 is shown to demonstrate how guidewire manipulation system 500 may interface with a robotic system, according to one embodiment. Instrument driver 560 may be draped with sterile drape 562, as shown. Drive shafts 505, 506 penetrate sterile barrier 562 and connect the motion of the motors in instrument driver 560 to guidewire manipulation system 500. In some embodiments, drive shafts 505, 506 may be part of a sterile adaptor, as described for example in U.S. Pat. No. 8,720,448. In the embodiments described above, guidewire manipulation system 200 may be attached to this instrument driver 560 in a similar manner. In alternative embodiments, drive shafts 505, 506 may form part of guidewire manipulation system 500 or instrument driver 560. Ideally, the connection of system 500 to the larger robotic surgery system with which it is used will be designed such that system 500 can be removed from the robotic surgery system while maintaining sterility of the surgical space.

The embodiment of guidewire manipulation system 500 illustrated in FIG. 7B is located immediately adjacent catheter splayer 564. This positioning of system 500 immediately next to splayer 564 may be advantageous, because when guidewire 550 is driven out of system 500, it immediately enters splayer 564, without risk of buckling. There is typically a valve (not shown) at the proximal end of catheter 566 in the location of splayer 564. The valve is designed to provide hemostasis, while allowing entry of guidewire 550. In alternative embodiments, it may be preferable to locate guidewire manipulation system 500 farther from splayer 564 to allow space for a drying, wiping, or cleaning mechanism (such as the drying, wiping, and cleaning mechanism described in US Publ. No. 2015/0297864, filed Apr. 21, 2015, issued as U.S. Pat. No. 10,046,140 on Aug. 14, 2018, and titled "Devices, Systems, and Methods for Controlling Active Drive Systems," the disclosure of which is herein incorporated by reference in its entirety). In some embodiments, the drying, wiping, or cleaning mechanism may be configured and used to dry the guidewire 550 before it reaches system 500. In other embodiments, it may not be necessary to dry the guidewire since the configurations described herein do not rely on friction; in such embodiments, the drying, wiping, or cleaning mechanism may still be present, for example, to clean the wire of blood to avoid the introduction or buildup of blood within the drum. In other alternative embodiments, guidewire manipulation system 500 may be incorporated into splayer 564, to reduce the number of component parts.

The mechanisms and methods described herein have broad applications. The foregoing embodiments were chosen and described in order to illustrate principles of the methods and apparatuses as well as some practical applications. The preceding description enables others skilled in the art to use methods and apparatus in various embodiments and with various modifications suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, this disclosure may be practiced otherwise than is specifically explained and illustrated, without departing from its spirit or scope. Various alternatives to the embodiments described herein may be employed in practicing the claims, without departing from the spirit and scope as defined in the following claims. The scope of the disclosure should be determined, not with reference to the above description, but instead with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A guidewire manipulation system for translating and rotating a flexible guidewire for a medical or surgical procedure, the system comprising:
   (a) a cylindrical drum, comprising:
      (i) a cylindrical outer drum surface with a helical groove for housing the flexible guidewire, the flexible guidewire configured to wrap around the cylindrical outer drum surface multiple times; and
      (ii) an anchoring mechanism for attaching the flexible guidewire to the cylindrical drum;
   (b) a layer disposed around the cylindrical drum, the layer configured to cover and prevent the flexible guidewire from lifting off of the cylindrical drum and defining an opening through which the flexible guidewire passes;
   (c) a first actuator coupled with the cylindrical drum for rotating the cylindrical drum about a first axis, to translate the flexible guidewire through the opening and along a longitudinal axis of the flexible guidewire; and
   (d) a second actuator coupled with the cylindrical drum for rotating the cylindrical drum to roll the flexible guidewire about the longitudinal axis, the second actuator being oriented parallel with the first actuator.

2. The system of claim 1, wherein the layer comprises a cylindrical shell configured to move axially along the cylindrical drum as the cylindrical drum is rotated.

3. The system of claim 2, further comprising:
   a cylindrical outer housing disposed over the cylindrical drum;
   a first tubular channel extending from a proximal end of the outer housing to a proximal edge of the cylindrical drum to guide the flexible guidewire from the proximal end of the outer housing to the proximal edge of the cylindrical drum; and
   a second tubular channel extending from a distal edge of the cylindrical drum to a distal end of the outer housing, to guide the flexible guidewire from the distal edge of the cylindrical drum to the distal end of the outer housing.

4. The system of claim 3, further comprising:
   a first guide tube for guiding the flexible guidewire from the proximal end of the outer housing to the helical groove at the proximal edge of the cylindrical drum; and
   a second guide tube for guiding the flexible guidewire from the helical groove at the distal edge of the cylindrical drum to the distal end of the outer housing.

5. The system of claim 1, further comprising:
   a cylindrical outer housing disposed over the cylindrical drum;
   a cylindrical barrel disposed between the outer housing and the cylindrical drum, wherein the cylindrical drum and the barrel are configured to rotate relative to the outer housing and to each other;
   a first drive shaft coupled with the cylindrical drum for rotating the cylindrical drum about a central axis of the cylindrical drum and the outer housing, to advance and retract the flexible guidewire along a longitudinal axis of the flexible guidewire; and
   a second drive shaft coupled with the barrel for rotating the barrel about the central axis to roll the flexible guidewire about the longitudinal axis.

6. The system of claim 5, wherein the cylindrical barrel comprises an inner threaded surface that meshes with a complementary outer threaded surface on the first drive shaft.

7. The system of claim 6, wherein the cylindrical drum is configured to move in a first direction within the cylindrical barrel when the system winds the flexible guidewire onto the cylindrical drum and in a second direction within the cylindrical barrel when the system unwinds the flexible guidewire off of the cylindrical drum.

8. The system of claim 1, wherein the layer is disposed around the helical groove of the cylindrical drum.

9. The system of claim 1, the first actuator being oriented coaxially with the longitudinal axis.

10. The system of claim 1, the second actuator being oriented coaxially with the longitudinal axis.

11. The system of claim 1, the first actuator being oriented coaxially with the second actuator.

12. The system of claim 11, the first actuator being coaxially nested within the second actuator.

13. The system of claim 11, the first and second actuators being oriented coaxially with the longitudinal axis.

14. The system of claim 1, the first and second actuators being oriented parallel with the longitudinal axis.

15. A guidewire manipulation system for translating and rotating a flexible guidewire for a medical or surgical procedure, the system comprising:
   (a) a cylindrical drum oriented along a longitudinal axis, comprising:
      (i) a cylindrical outer drum surface with a helical groove for housing the flexible guidewire, the flexible guidewire configured to wrap around the cylindrical outer drum surface multiple times; and
      (ii) an anchoring mechanism for attaching the flexible guidewire to the cylindrical drum;
   (b) a layer disposed around the cylindrical drum and extending along the longitudinal axis, the layer configured to cover and prevent the flexible guidewire from lifting off of the cylindrical drum and defining an opening through which the flexible guidewire passes;
   (c) a first actuator extending along the longitudinal axis, the first actuator being coupled with the cylindrical drum for rotating the cylindrical drum about a first axis, to translate the flexible guidewire through the opening and along the longitudinal axis; and
   (d) a second actuator extending along the longitudinal axis, the second actuator being coupled with the cylindrical drum for rotating the cylindrical drum about the longitudinal axis, to thereby roll the flexible guidewire about the longitudinal axis.

16. A guidewire manipulation system for translating and rotating a flexible guidewire for a medical or surgical procedure, the system comprising:

(a) a cylindrical drum, comprising:
  (i) a cylindrical outer drum surface with a helical groove for housing the flexible guidewire, the flexible guidewire configured to wrap around the cylindrical outer drum surface multiple times; and
  (ii) an anchoring mechanism for attaching the flexible guidewire to the cylindrical drum;
(b) a layer disposed around the cylindrical drum, the layer configured to cover and prevent the flexible guidewire from lifting off of the cylindrical drum and defining an opening through which the flexible guidewire passes;
(c) a first actuator coupled with the cylindrical drum for rotating the cylindrical drum, to translate the flexible guidewire through the opening and along a longitudinal axis of the flexible guidewire; and
(d) a second actuator coupled with the cylindrical drum for rotating the cylindrical drum, to roll the flexible guidewire about the longitudinal axis, the first actuator being coaxially nested within the second actuator.

* * * * *